United States Patent
Wang et al.

(10) Patent No.: US 12,094,581 B2
(45) Date of Patent: Sep. 17, 2024

(54) SYSTEMS FOR GENERATING PERSONALIZED AND/OR LOCAL WEATHER FORECASTS

(71) Applicant: Micron Technology, Inc., Boise, ID (US)

(72) Inventors: Libo Wang, Boise, ID (US); Xiao Li, Boise, ID (US); Bethany M. Grentz, Meridian, ID (US); Sumana Adusumilli, Boise, ID (US); Carla L Christensen, Boise, ID (US)

(73) Assignee: Micron Technology, Inc., Boise, ID (US)

( * ) Notice: Subject to any disclaimer, the term of this patent is extended or adjusted under 35 U.S.C. 154(b) by 628 days.

(21) Appl. No.: 16/993,175

(22) Filed: Aug. 13, 2020

(65) Prior Publication Data

US 2022/0051765 A1   Feb. 17, 2022

(51) Int. Cl.
G16H 10/60 (2018.01)
G01W 1/10 (2006.01)
G16H 20/70 (2018.01)

(52) U.S. Cl.
CPC .............. *G16H 10/60* (2018.01); *G01W 1/10* (2013.01); *G16H 20/70* (2018.01); *G01W 2203/00* (2013.01)

(58) Field of Classification Search
CPC .......... G01K 13/20; G01W 1/02; G01W 1/10; G01W 1/17; G01W 2001/006;

(Continued)

(56) References Cited

U.S. PATENT DOCUMENTS

| | | |
|---|---|---|
| 6,542,407 B1 | 4/2003 | Chen et al. |
| 9,158,672 B1 | 10/2015 | Zheng et al. |

(Continued)

FOREIGN PATENT DOCUMENTS

| | | |
|---|---|---|
| CN | 106663460 A | 5/2017 |
| CN | 111383676 A | 7/2020 |

OTHER PUBLICATIONS

CN Patent Application No. 202111030864.4—Chinese Office Action and Search Report, dated Jan. 22, 2024, with English Translation, 9 pages.

*Primary Examiner* — Yoshihisa Ishizuka
(74) *Attorney, Agent, or Firm* — Perkins Coie LLP

(57) ABSTRACT

Systems for weather sensing and forecasting, and associated devices and methods, are disclosed herein. In some embodiments, a system for predicting a subject's perception of weather conditions is provided. The system can generate an individual profile for the subject, the individual profile including health information of the subject. The system can receive weather data including a first weather condition for a target location. The system can compare the individual profile to a plurality of different user profiles to identify one or more similar user profiles. Each similar user profile can (1) be associated with a user having similar health information as the subject, and (2) include weather perception data indicating how the user perceived a set of second weather conditions. Based on the weather data and the similar user profile(s), the system can generate a prediction of the how the subject will perceive the first weather condition.

14 Claims, 5 Drawing Sheets

(58) Field of Classification Search
CPC ... G01W 2203/00; G16H 10/60; G16H 20/70; G16H 50/20; Y02A 90/10
See application file for complete search history.

(56) References Cited

U.S. PATENT DOCUMENTS

| | | |
|---|---|---|
| 10,825,567 B1* | 11/2020 | Wala ..................... G16H 10/20 |
| 2013/0053990 A1* | 2/2013 | Ackland ............ A61B 5/02055 |
| | | 700/91 |
| 2015/0357023 A1 | 12/2015 | Hush |
| 2016/0171110 A1* | 6/2016 | Gao ........................ G06F 16/29 |
| | | 707/722 |
| 2017/0287547 A1 | 10/2017 | Ito et al. |
| 2019/0056874 A1 | 2/2019 | Lee et al. |
| 2020/0211626 A1 | 7/2020 | Hiscock et al. |
| 2022/0076731 A1 | 3/2022 | Rooney |

* cited by examiner

SYSTEMS FOR GENERATING PERSONALIZED AND/OR LOCAL WEATHER FORECASTS

TECHNICAL FIELD

The present technology generally relates to systems for weather sensing and forecasting, and more particularly relates to systems for generating personalized weather forecasts and/or forecasting local weather conditions.

BACKGROUND

Weather forecasting services provide predictions of weather conditions such as temperature, precipitation, and humidity. However, it may be difficult for an individual to determine how these predictions correlate to their own subjective perception of the weather, particularly when the prediction is expressed quantitatively (e.g., as a specific temperature value). These difficulties are compounded by the fact that different individuals may perceive the same weather conditions differently. Additionally, weather forecasting services generally provide predictions for a larger geographic region, which may not be representative of local weather conditions for specific locations or sub-areas within that region.

BRIEF DESCRIPTION OF THE DRAWINGS

Many aspects of the present technology can be better understood with reference to the following drawings. The components in the drawings are not necessarily to scale. Instead, emphasis is placed on illustrating clearly the principles of the present technology.

DETAILED DESCRIPTION

Figure 1:
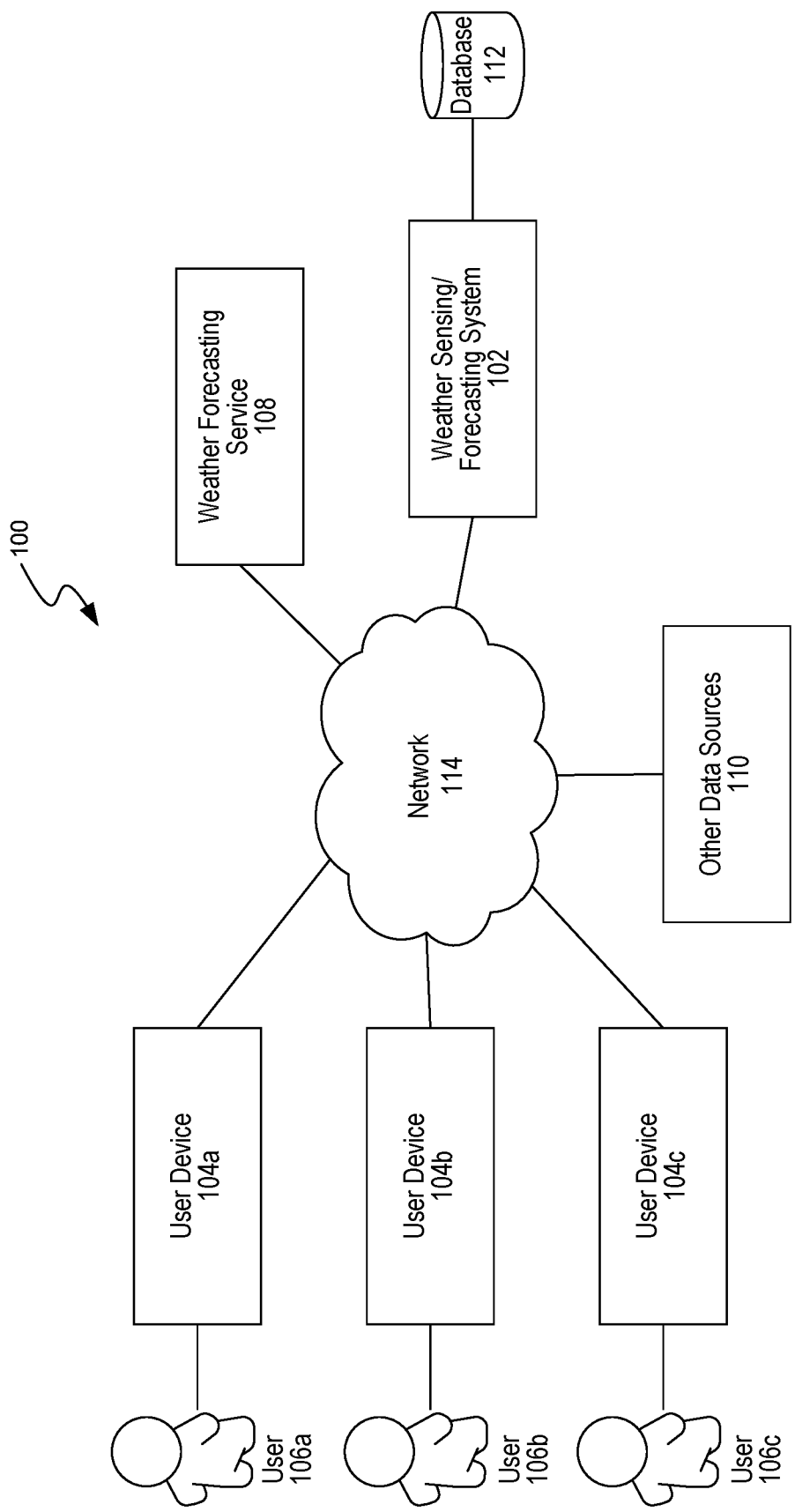
FIG. 1 is a network diagram illustrating an exemplary computing environment in which a weather sensing and forecasting system operates, in accordance with embodiments of the present technology.

The present technology provides systems for weather sensing and forecasting, and associated devices and methods. In some embodiments, for example, a system for predicting a subject's perception of weather conditions is provided. The system can generate an individual profile for the subject, the individual profile including health information of the subject (e.g., age, gender, health status, etc.). The system can receive weather data including a first weather condition (e.g., temperature, humidity, cloud coverage, wind speed) for a target location. The system can compare the individual profile to a plurality of different user profiles to identify one or more similar user profiles. Each similar user profile can (1) be associated with a user having similar health information as the subject, and (2) include weather perception data indicating how the user perceived a set of second weather conditions. Based on the weather data and the similar user profile(s), the system can generate a prediction of the how the subject will perceive the first weather condition (also referred to herein as a "personalized weather forecast"). For example, the system can generate a prediction of the degree of coldness, warmth, humidity, dryness, sunniness, brightness, windiness, etc. that the subject would feel when exposed to the at least one weather condition. Optionally, the system can generate the prediction by inputting the weather data and individual profile into a machine learning model that is trained on the plurality of different user profiles. The techniques described herein can provide personalized weather forecasts that accurately predict how a particular subject would actually feel when exposed to different weather conditions, thus assisting the subject in preparing for weather-influenced activities (e.g., outdoor recreation, trip planning, etc.).

In another aspect of the present technology, a system for generating a weather forecast for a target location is provided. The system can receive regional weather data for a region that at least partially encompasses the target location. For example, the regional weather data can be received from a weather station or weather forecasting service. The system can also receive local data from a plurality of different local devices at or near the target location. The different local devices can include at least one wearable device (e.g., a smartwatch, fitness monitor). Optionally, the different local devices can include a mobile device (e.g., a smartphone), a sensor carried by a vehicle (e.g., an automobile, autonomous vehicle), and/or a sensor associated with a building (e.g., a smart thermostat). The system can generate the weather forecast for the target location based on the regional weather data and the local data. For example, the system can use the local data to estimate local weather conditions at the target location, and can combine the estimated local weather conditions with the regional weather data to determine the weather forecast for the target location. This approach can improve the accuracy of weather forecasts, particularly for target locations and/or smaller areas within a larger region.

Numerous specific details are disclosed herein to provide a thorough and enabling description of embodiments of the present technology. A person skilled in the art, however, will understand that the technology may have additional embodiments and that the technology may be practiced without several of the details of the embodiments described below with reference to FIGS. 1-5. For example, some details of structures or functions well known in the art have been omitted so as not to obscure the present technology. In general, it should be understood that various other devices and systems in addition to those specific embodiments disclosed herein may be within the scope of the present technology.

As used herein, the phrase "and/or" as in "A and/or B" refers to A alone, B alone, and A and B.

The headings provided herein are for convenience only and do not interpret the scope or meaning of the claimed present technology.

A. Systems and Devices for Weather Sensing and Forecasting

FIG. 1 is a network diagram illustrating an exemplary computing environment 100 in which a weather sensing and forecasting system 102 operates, in accordance with embodiments of the present technology. The system 102 is configured to perform various weather-related operations, such as predicting individual perceptions of weather conditions and/or generating local weather forecasts, as described in greater detail below with respect to FIGS. 3-5. The system 102 can be implemented as a special purpose computer or data processor that is specifically programmed, configured, or constructed to perform one or more of the operations explained in detail herein. Indeed, the term "computer" and "computing device," as used generally herein, refer to devices that have a processor and non-transitory memory, as well as any data processor or any device capable of communicating with a network. Data processors can include programmable general-purpose or special-purpose microprocessors, programmable controllers, application-specific integrated circuits (ASICs), programming logic devices (PLDs), or the like, or a combination of such devices.

The system 102 is operably coupled to a plurality of user devices 104a-c (collectively, "user devices 104") that are respectively associated with a plurality of users 106a-c (collectively, "users 106"). The user devices 104 can be or include any device capable of receiving, processing, storing, and outputting data, such as a wearable device, mobile device, laptop computer, tablet, personal computer, or any other suitable computing device. In some embodiments, some or all of the user devices 104 can include at least one sensor for automatically or semi-automatically collecting biometric data and/or other user data. Alternatively or in combination, the users 106 can manually input data into the user devices 104.

The users 106 can operate the user devices 104 to interact with the system 102. For example, the user devices 104 can send data to the system 102, such as user data, sensor data, requests (e.g., requests for weather forecasts), and the like. Data can be sent automatically (e.g., at predetermined time intervals, upon receipt of new or updated data by the user device 104), manually (e.g., when a user 106 instructs the user device 104 to send a request or other data), or a combination thereof. The user devices 104 can also output data received from the system 102 (e.g., forecasts, notifications, recommendations) for display to the users 106. Additional details of the components and functions of the user devices 104 are discussed below with respect to FIG. 2.

In some embodiments, the system 102 is configured to communicate with at least one weather forecasting service 108. The weather forecasting service 108 can be a government agency, a commercial enterprise, a weather monitoring facility (e.g., a weather station), or any other third party entity that provides weather data. The weather data provided by the weather forecasting services 108 can include data regarding any of the following weather conditions: temperature (e.g., average, high, low, and/or hourly temperatures), apparent temperature (e.g., a "feels like" temperature value), precipitation (e.g., amount, type (such as rain, snow, hail, showers, thunderstorms, etc.)), humidity, wind speed, wind chill, dew point, pressure, UV index, visibility, air quality, cloud conditions (e.g., sunny, mostly sunny, partly sunny, partly cloudy, mostly cloudy, cloudy), presence of fog, emergency conditions (e.g., windstorms, severe thunderstorms, tornadoes), and the like. Weather data can include data of current weather conditions, historical weather conditions (e.g., past hour, past 12 hours, past 24 hours, past 48 hours, past month, etc.), and/or predicted future weather conditions (e.g., next hour, next 12 hours, next 24 hours, next 48 hours, next 3 days, next 10 days, next month, etc.). Predictions of future weather conditions can be expressed quantitively (e.g., "10% chance of rain") and/or qualitatively (e.g., "slight chance of rain").

Optionally, the system 102 can also communicate with one or more other data sources 110. The other data sources 110 can include any system, device, or entity that provides data relevant to weather sensing and forecasting. For example, the other data sources 110 can include one or more sensors that are carried by a vehicle (e.g., an automobile, an autonomous vehicle), associated with a building (e.g., a residential building such as a user's home, a commercial building), at a fixed location within the environment, or any other suitable arrangement. The sensors can include weather sensors configured to directly measure weather and/or environmental conditions, such as a temperature sensor, a wind sensor (e.g., wind speed sensor, wind direction sensor), precipitation sensor, pressure sensor, humidity sensor, air quality sensor, brightness or sunlight sensor, oxygen sensor, UV sensor, altitude sensor, and so on. Optionally, some sensors can be configured to measure a parameter that may be used to indirectly estimate weather conditions. For example, sensors located within a building may provide data that indirectly correlates with outside weather conditions (e.g., operation of an air conditioning system may indicate high temperatures outside, operation of a heating system may indicate low temperatures outside).

In some embodiments, the other data sources 110 can provide other types of data relevant to the techniques described herein, such as user data. For example, the other data sources 110 can include a system or device associated with a healthcare provider that stores health information for one or more of the users 106 (e.g., in the form of electronic medical records, health reports, etc.). The system 102 can retrieve the health information directly from the healthcare provider, such that the users 106 do not need to manually input the health information into the user devices 104. In other embodiments, however, some types of health information may be retrieved directly from the healthcare provider (e.g., medical records and reports), while other types of health information may be transmitted to the system 102 from the user devices 104 (e.g., biometric sensor data) as discussed in greater detail below. Health information can be retrieved from the system at predetermined time intervals, when updated information is available, when an authorization or request is received from the user devices 104, etc.

The system 102 can store data received from the user devices 104, weather forecasting service 108, and/or other data sources 110 in one or more databases 112. The databases 112 can also store data generated by the system 102, such as weather forecasts, user profiles, recommendations, notifications, etc. In some embodiments, the system 102 converts data received from different sources into a standardized format to facilitate storage and data processing. For example, data from different weather forecasting services 108 and/or different data sources 110 can include different types of information and/or be in different formats. Additionally, user data from different user devices 104 can include different types of information (e.g., different types of sensor data) and/or be in different formats (e.g., depending on the hardware and/or software platform used). In some embodiments, the system 102 generates a user profile for each user 106, the user profile storing user information in a standardized format suitable for user in the operations performed by the system 102 (e.g., comparison with other user profiles, input into machine learning models or other algorithms, etc.). As discussed in greater detail below, the user profile can include various types of user information, such as health information, location information, personal information, weather perception data, previous personalized weather forecasts generated for that user, etc. Optionally, data that contains sensitive user information (e.g., health information, biometric information) can be anonymized and/or encrypted for compliance with privacy standards.

In the illustrated embodiment, the system 102 is operably coupled to the user devices 104, weather forecasting service 108, and other data sources 110 via a network 114. The network 114 can be or include one or more communications networks, and can include at least one of the following: a wired network, a wireless network, a metropolitan area network ("MAN"), a local area network ("LAN"), a wide area network ("WAN"), a virtual local area network ("VLAN"), an internet, an extranet, an intranet, and/or any other type of network and/or any combination thereof. Additionally, although FIG. 1 illustrates the system 102 as being directly connected to the database 112 without the network 114, in other embodiments the system 102 can be indirectly connected to the database 112 via the network 114. Moreover, any of the user devices 104, weather forecasting service 108, and/or other data sources 110 can be configured to communicate directly with the system 102 (e.g., via wired or wireless connections), rather than communicating indirectly via the network 114.

One of skill in the art will appreciate that the components illustrated in FIG. 1 can have many different configurations. For example, although FIG. 1 illustrates three user devices 104a-c and three users 106a-c, the system 102 can be connected to any number of user devices 104 and users 106 (e.g., tens, hundreds, thousands, tens of thousands, etc.). Additionally, some users 106 can be associated with more than one user device 104 (e.g., a single user 106 can have both a wearable device and a mobile device) and/or a single user device 104 may be associated with more than one user 106 (e.g., multiple family members can share the same user device 104).

Moreover, although the system 102 is illustrated as being a single component, in other embodiments, aspects of the system 102 can be practiced in distributed computing environments, where tasks or modules are performed by remote processing devices, which are linked through a communications network (e.g., network 114). In a distributed computing environment, program modules or subroutines may be located in both local and remote memory storage devices. Aspects of the system 102 described herein may be stored or distributed on tangible, non-transitory computer-readable media, including magnetic and optically readable and removable computer discs, stored in firmware in chips (e.g., EEPROM chips). Alternatively or in combination, aspects of the system 102 may be distributed electronically over the Internet or over other networks (including wireless networks). Those skilled in the relevant art will recognize that portions of the system 102 may reside on a server computer, while corresponding portions reside on a client computer. Some or all of the operations described herein can be performed entirely by the system 102 or entirely by a user device 104, or can be performed by both the system 102 and at least one user device 104. For example, more urgent operations can be performed locally on the user device 104 (e.g., generating notifications or alerts), while more complex operations can be performed remotely by the system 102 (e.g., generating predictions and forecasts).

Figure 2:
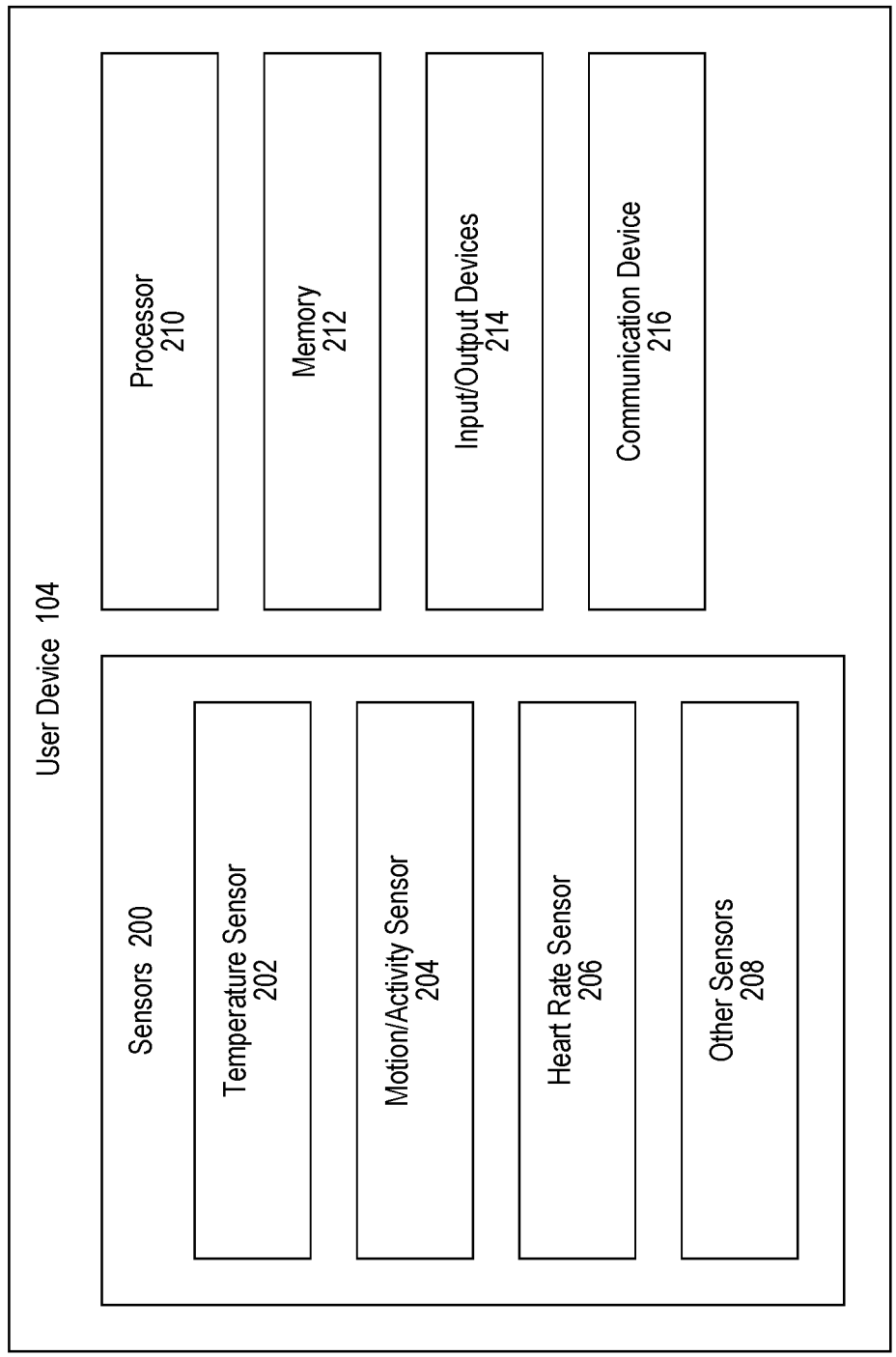
FIG. 2 is a schematic illustration of a user device configured in accordance with embodiments of the present technology.

FIG. 2 is a schematic illustration of a user device 104 configured in accordance with embodiments of the present technology. The user device 104 can include one or more sensors 200, a processor 210 (e.g., programmable general-purpose or special-purpose microprocessor, programmable controller, ASIC, PLD), a memory 212 (e.g., SRAM, DRAM, flash, and/or other memory devices), input/output devices 214 (e.g., touchscreen, monitor, keyboard, mouse, joystick, stylus, microphone, camera), and a communication device 216 (e.g., for communicating with external devices such as the system 102 of FIG. 1). The user device 104 can be a wearable device (e.g., smartwatch, fitness monitor, smart glasses), mobile device (e.g., smartphone), laptop computer, tablet, personal computer, or other computing device.

In embodiments where the user device 104 is a wearable device, the user device 104 can be worn on, connected to, or otherwise carried by any part of the user's body, such as a finger, hand, wrist, arm, shoulder, torso, head, ear, neck, waist, hip, leg, ankle, foot, etc. Alternatively or in combination, the user device 104 can be configured to be attached to, placed within, or otherwise carried by the user's clothing, such as headgear, shirt, pants, gloves, socks, footwear, glasses, belt, headband, wristband, outerwear, etc. The user device 104 can include straps, bands, loops, buckles, clips, or other fasteners suitable for attaching the user device 104 to the user's body and/or clothing.

The user device 104 can be used to collect various types of user information, such as health information. Health information can include, but is not limited to, any of the following: age, gender, demographics, weight, height, body mass index (BMI), body fat percentage, cardiovascular data (e.g., heart rate, blood pressure, blood flow), respiratory rate, body temperature (e.g., skin temperature), gender-specific data (e.g., menstrual status, pregnancy status), medical history, familial medical history, diseases or conditions (e.g., hypertension, hyperlipidemia, heart failure, asthma, lung disease, allergies, fever, migraines, arthritis, mood disorders), and so on. The user device 104 can also collect other types of relevant information from the user, such as location information, personal information, etc.

The user information can be provided to the user device 104 in various ways. In some embodiments, the user manually inputs user information into the user device 104 via the input/output devices 214. Alternatively or in combination, the user device 104 can semi-automatically or automatically collect user information, e.g., via one or more sensors 200. For example, the sensors 200 can include at least one biometric sensor configured to obtain health information and/or biometric data, such as a temperature sensor 202 configured to measure the user's body temperature (e.g., skin temperature), a motion or activity sensor 204 (e.g., an accelerometer, gyroscope, pedometer) configured to measure user movement (e.g., walking, running, resting), and/or a heart rate sensor 206. The sensors 200 can alternatively or additionally include other sensors 208 configured to measure other biometric parameters, such as perspiration, piloerection (goosebumps), respiratory rate, blood pressure, blood flow, etc. Optionally, the other sensors 208 can measure other types of parameters that may be relevant to the weather forecasting techniques described herein, such as weather sensors, location sensors (e.g., GPS sensors), image sensors (e.g., cameras), audio sensors (e.g., microphones), and so on. For example, images of a user can be analyzed using computer vision techniques to estimate the corresponding weather conditions, e.g., by identifying environmental objects (e.g., snow, rain, clear skies), clothing worn by the user and/or other individuals in the image, etc.

Although FIG. 2 illustrates the sensors 200 as being part of the user device 104, in other embodiments, some or all of the sensors 200 can instead be part of a separate device that is in communication with the user device 104 (e.g., via the communication device 216). For example, some or all of the sensors 200 can be part of a wearable device (e.g., smartwatch, fitness monitor) that communicates with the user device (e.g., a mobile device, tablet, laptop computer) via wired or wireless communication methods. In such embodiments, the sensors 200 can transmit sensor data to the user device 104 (e.g., automatically and/or in response to requests from the user device 104), and the user device 104 can process and store the received sensor data. The user device 104 can also transmit commands or other control signals to the sensors 200 (e.g., to trigger the sensors 200 to collect data).

B. Methods for Weather Sensing and Forecasting

Figure 3:
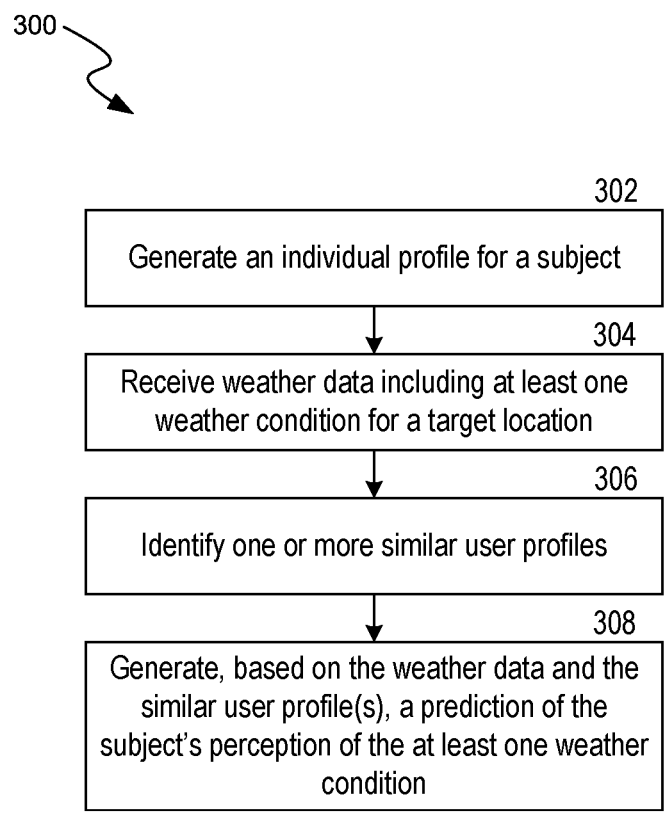
FIG. 3 is a flow diagram illustrating a method for predicting a subject's perception of weather conditions, in accordance with embodiments of the present technology.
Figure 4:
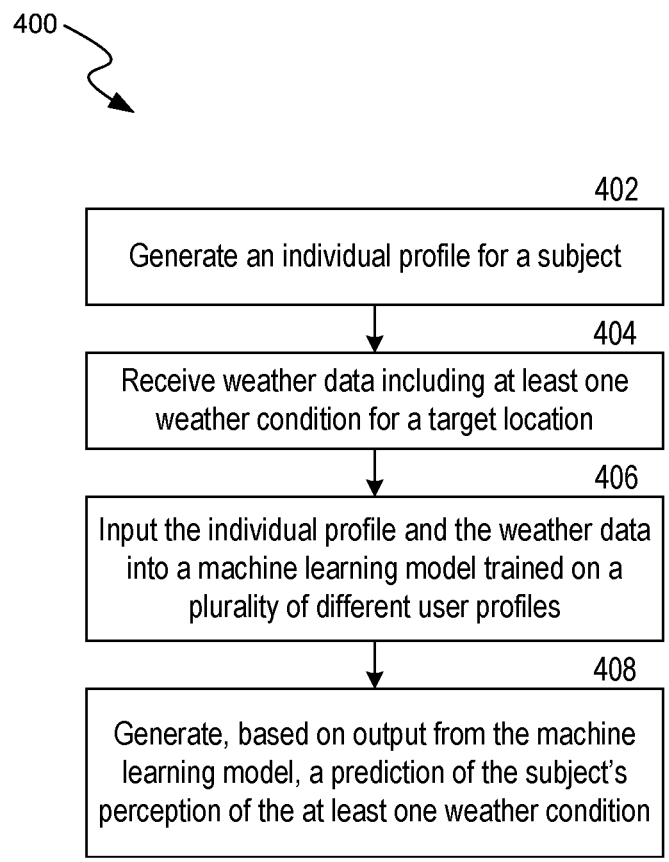
FIG. 4 is a flow diagram illustrating another method for predicting a subject's perception of weather conditions, in accordance with embodiments of the present technology.
Figure 5:
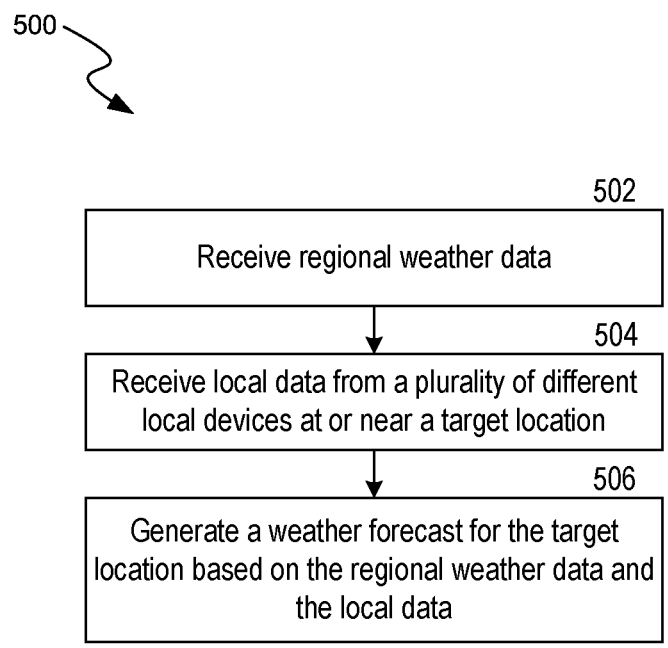
FIG. 5 is a flow diagram illustrating a method for generating a weather forecast for a target location, in accordance with embodiments of the present technology.

FIGS. 3-5 illustrate various methods for weather sensing and forecasting that can be performed by any of the systems and devices described herein, such as the system 102 of FIG. 1, the user device 104 of FIGS. 1 and 2, or a combination thereof. In some embodiments, some or all of the operations described with respect to FIGS. 3-5 are implemented as computer-executable instructions, such as routines executed by a general-purpose computer, a personal computer, a server, or other computing system. Computer-executable instructions may be stored in memory, such as random access memory (RAM), read-only memory (ROM), flash memory, or the like, or a combination of such components. Computer-executable instructions may also be stored in one or more storage devices, such as magnetic or optical-based disks, flash memory devices, or any other type of non-volatile storage medium or non-transitory medium for data. Computer-executable instructions may include one or more program modules, which include routines, programs, objects, components, data structures, and so on that perform particular tasks or implement particular abstract data types.

FIG. 3 is a flow diagram illustrating a method 300 for predicting a subject's perception of weather conditions, in accordance with embodiments of the present technology. As discussed above, a conventional weather forecast (e.g., "60° F., partly cloudy") may not provide sufficient information for a particular subject to determine how they would feel when exposed to the actual weather conditions. Even if the weather forecast includes an apparent temperature value (e.g., "feels like 55° F."), this value may be a generic estimate that is not customized to the particular subject. Moreover, different individuals may perceive the same weather conditions differently (e.g., based on factors such as age, gender, weight, health conditions, etc.), such that a single apparent temperature value is unlikely to accurately reflect the particular subject's actual perceived temperature. The method 300 can address these and other challenges by generating a personalized weather forecast that predicts the subject's actual perception of weather conditions.

The method 300 begins at block 302 with generating an individual profile for a subject. The individual profile can include various types of information about the subject, such as health information (e.g., age, gender, weight, blood pressure, menstrual status, pregnancy status, etc.), location information (e.g., GPS coordinates), personal information, and the like. As previously discussed with respect to FIGS. 1 and 2, health information and/or other information about the object can be obtained via a user device (e.g., user device 104) and can be used to generate an individual profile for the subject. In some embodiments, the individual profile is generated in a standardized format so the profile can be easily compared to other user profiles, as discussed in detail below. The individual profile can be generated locally by a user device (e.g., user device 104 of FIGS. 1 and 2), by a remote device (e.g., system 102 of FIG. 1), or any suitable combination thereof. For example, the individual profile can be generated locally on the user device and subsequently transmitted to the system, or vice-versa.

In some embodiments, the individual profile further includes data indicating how the subject perceived one or more weather conditions, also referred to herein as "weather perception data." For example, the weather perception data can indicate the degree of perceived coldness, warmth, humidity, dryness, sunniness, brightness, windiness, etc. when the subject was exposed to various weather conditions. In some embodiments, the weather perception data includes a plurality of data sets, each data set including (i) data representing one or more weather conditions and (ii) data representing how the subject perceived those weather conditions. The subject's perception can be expressed quantitively (e.g., as a value or score), qualitatively (e.g., "cold," "hot," "uncomfortable," "comfortable"), or combinations thereof. As discussed above, weather conditions can encompass, for example, different temperatures (e.g., hot, warm, cool, cold), types of precipitation (e.g., rain, snow, hail, sleet, showers, rain, thunderstorm), wind speeds, cloud coverage (e.g., sunny, mostly sunny, partly sunny, partly cloudy, mostly cloudy, cloudy), and the like.

The weather perception data can be generated in various ways, such as automatically (e.g., using one or more sensors as previously described with respect to FIG. 2), manually (e.g., via user input), or a combination thereof. For example, the subject can input their perception of a particular weather condition while and/or after they are exposed to the condition. Alternatively or in combination, the subject's perception can be estimated using biometric sensor data, such as by measuring the subject's body temperature, sweating, blood pressure, heart rate, respiratory rate, shivering, etc. Optionally, the estimate can be displayed to the subject for approval, rejection, or modification before being saved to the individual profile.

In some embodiments, when the subject initially enrolls in the system, the system prompts the subject to record their responses to different weather conditions in order to create an initial set of weather perception data, also referred to herein as "calibration data." The calibration data can be used to predict the subject's perception of future weather conditions, as discussed in detail below. Optionally, the calibration data can subsequently be updated to include additional weather perception data, reflect changes in the subject's perception over time, etc.

At block 304, weather data is received. The weather data can be provided by a third party source such as a weather forecasting service (e.g., the weather forecasting service 108 of FIG. 1), or can be provided by the system itself (e.g., the system 102 of FIG. 1). The weather data can include any suitable data regarding one or more weather conditions at a target location, such as temperature, precipitation, humidity, cloud cover, etc. The weather condition can be a current weather condition or a predicted future weather condition. In some embodiments, the weather data is associated with time information such as a time stamp. Optionally, the user can input a time frame of interest for the forecast, and the system requests or retrieves weather data that falls within the time frame. The target location for the weather data can be a current location of the subject, a potential future location of the subject, or a location that is otherwise of interest. The target location can be specified by a set of coordinates (e.g., GPS coordinates), a street address, a name of a building or landmark, a neighborhood, a town, a city, a county, an area code, or any other suitable indicator. In some embodiments, the subject inputs the target location via a graphical user interface, e.g., by entering the name or address of the location, selecting a location on a displayed map, or any other suitable method.

At block 306, one or more similar user profiles are identified. The similar user profile(s) can be profiles of other users (e.g., users 106 of FIG. 1) that have at least some characteristics that are identical or similar to the corresponding characteristics of the subject. For example, the similar user profile(s) can be associated with users having similar health information (e.g., age, gender, weight, etc.) and/or other information (e.g., personal information) as the subject. Alternatively or in combination, the similar user profile(s) can be associated with users that perceive weather conditions similarly as the subject, e.g., having similar weather perception data and/or calibration data. The similar user profile(s) can be identified using various techniques. For example, the system can compare the subject's individual profile to a plurality of different user profiles to identify the similar user profile(s). In some embodiments, the comparison includes generating a similarity score for each user profile that indicates the degree of similarity with the individual profile, and selecting user profiles based on the similarity score. In some embodiments, some characteristics can be weighted differently in determining the similarity score, e.g., gender can be weighted more heavily than age. Optionally, machine learning-based techniques can be used to identify similar user profiles, as discussed in greater detail below with respect to FIG. 4.

At block 308, a prediction of the subject's perception of the at least one weather condition is generated, based on the weather data and the similar user profile(s). The prediction can be generated in many different ways. For example, in some embodiments, the similar user profile(s) identified in block 306 each include weather perception data indicating how the corresponding user felt when exposed to one or more weather conditions. The system can analyze the weather perception data from each similar user profile to identify instances where that user was exposed to conditions that were the same or similar as the at least one weather condition, and can determine how that user perceived those conditions. Subsequently, weather perception data from multiple instances and/or users can be averaged, aggregated, or otherwise combined to generate the prediction for the current subject. Optionally, weather perception data from different users can be weighted differently, e.g., data from users that are highly similar to the subject can be weighted more heavily than data from users that are less similar to the subject.

Alternatively or in combination, the system can identify similar users that are currently at the target location and/or were recently at the target location (e.g., within the last 5 minutes, 10 minutes, 30 minutes, 1 hour, 2 hours, etc.). For example, the system can analyze location information from multiple users to determine which users are or were at the target location, and/or within a predetermined distance from the target location. The system can then average, aggregate, or otherwise combine the weather perception data from users at or near the target location to predict how the current subject is likely to perceive the weather conditions at the target location.

Optionally, the prediction can be generated using previous weather perception data (e.g., calibration data) of the subject. For example, the system can analyze the subject's previous weather perception data to identify instances where that subject was exposed to the same or similar weather conditions, and determine how the subject perceived those conditions. The system can average, aggregate, interpolate, extrapolate, or otherwise analyze the previous weather perception data to generate the prediction for the current weather condition of interest. In some embodiments, the previous weather perception data can be weighted differently based on time and/or similarity to the current weather conditions of interest, e.g., more recent and/or similar data can be weighted more heavily than older and/or dissimilar data.

Subsequently, the prediction can be displayed to the subject, such as via a graphical user interface on a user device (e.g., a mobile device). As described above, the prediction can indicate how the subject would perceive the weather condition at the target location. In some embodiments, the prediction indicates the degree of perceived coldness, warmth, humidity, dryness, sunniness, brightness, windiness, etc. that the subject is likely to feel when exposed to the weather condition. The prediction can be expressed quantitatively, qualitatively, or a combination thereof. Optionally, once the subject actually experiences the weather condition, the subject can record their actual weather perception and/or provide an accuracy rating for the prediction, which can be used as input for generating future predictions.

In some embodiments, the prediction is used to generate notifications, alerts, recommendations, and/or other messages that are output to the subject. For example, based on the prediction, the system can generate a notification of how the subject is likely to perceive the weather conditions at the target location (e.g., "It's going to be very chilly at Bogus Basin") and/or a recommended action that the subject should take to prepare for those conditions, such as recommended clothing (e.g., "Bring a warm coat, hat, and gloves") and/or other preparations (e.g., "Wear sunscreen"). Optionally, if the subject has a health condition that may put them at risk when exposed to the weather conditions, the system can output an appropriate alert and/or recommendation (e.g., "Cold weather may trigger an asthma attack, don't forget your inhaler," "Power outages may occur during severe thunderstorms, make sure you have a backup power supply for your oxygen equipment"). Output data can be displayed via a graphical user interface on a user device, or provided in other formats (e.g., audible alerts, vibrations, etc.). Optionally, notifications or other messages can also be sent to family members, health care aides, caretakers and/or other individuals associated with the subject.

FIG. 4 is a flow diagram illustrating a method 400 for predicting a subject's perception of weather conditions, in accordance with embodiments of the present technology. The method 400 can be performed in combination with or as an alternative to the method 300 of FIG. 3. The method 400 begins with generating an individual profile for a subject (block 402) and receiving weather data including at least one weather condition for a target location (block 404). The processes of blocks 402 and 404 can be identical or generally similar to the processes described above with respect to blocks 302 and 304 of FIG. 3.

At block 406, the individual profile and the weather data are input into a machine learning model. The machine learning model can be trained on a plurality of different user profiles (e.g., hundreds, thousands, tens of thousands of user profiles) to predict how the subject would feel when exposed to various weather conditions. Optionally, the machine learning model can also be trained on the subject's individual profile (e.g., based on calibration data or other weather perception data of the subject). The machine learning model can be implemented in various ways. In some embodiments, for example, the machine learning model is trained to identify one or more user profiles that are similar to the individual profile (e.g., have similar characteristics and/or are likely to perceive weather similarly as the subject). Alternatively or in combination, the machine learning model can be trained to determine associations between the subject's characteristics (e.g., health information) and the subject's perception of weather conditions. The machine learning model can include any suitable type of model, such as supervised learning models, unsupervised learning models, semi-supervised learning models, and/or reinforcement learning models. Examples of machine learning models suitable for use with the present technology include, but are not limited to: artificial neural networks, deep learning algorithms, clustering algorithms, association rule learning algorithms, dimensionality reduction algorithms, regression algorithms, instance-based algorithms, regularization algorithms, decision tree algorithms, Bayesian algorithms, time series forecasting algorithms, and ensemble algorithms.

At block 408, a prediction of the subject's perception of the at least one weather condition is generated, based on output from the machine learning model. In some embodiments, the machine learning model directly outputs the prediction, which can be a value (e.g., a score representing the degree of perceived coldness, warmth, humidity, dryness, sunniness, brightness, windiness, etc.), a category or state (e.g., "hot," "warm," "cold"), or a combination thereof. In other embodiments, the machine learning model can output data that is then used to generate the final prediction. For example, the machine learning model can output a set of similar user profiles, and the similar user profiles can then be analyzed to produce the prediction, as previously discussed. The prediction can be subsequently displayed to the subject, as described above with respect to block 308 of FIG. 3.

The personalized weather forecasts described herein with respect to FIGS. 3 and 4 can be integrated into a wide variety of applications. For example, the forecasting techniques described herein can be implemented by a mobile app or other software for planning events, trips, outdoor activities, or the like. In such embodiments, the subject can input one or more target locations and/or times into the app (e.g., locations and/or dates for an event, trip, activity, etc.) and the app can generate a personalized weather forecast for the subject for each of the target locations at the target times. Optionally, personalized weather forecasts can be generated for multiple individuals (e.g., family members).

FIG. 5 is a flow diagram illustrating a method 500 for generating a weather forecast for a target location, in accordance with embodiments of the present technology. As discussed above, weather forecasts for a large geographic region may not be representative of local weather conditions for a smaller target location within that region. The method 500 can improve the accuracy of weather forecasts for a target location by using data from multiple local sources at or near the location to estimate local weather conditions.

The method 500 begins at block 502 with receiving regional weather data. The regional weather data can include one or more weather conditions for a relatively large geographic region, such as a city, county, area code, etc. In some embodiments, the regional weather data is received from a weather forecasting service (e.g., weather forecasting service 108 of FIG. 1), such as a government agency, a commercial enterprise, a weather station, or other third party provider of weather data. The weather data can include past, present, and/or predicted future weather conditions (e.g., conditions within the next 30 minutes, 1 hour, 2 hours, etc.).

At block 504, local data is received from a plurality of local devices at or near a target location. The target location can be a location or sub-region that is partially or entirely encompassed by the larger geographic region. For example, if the geographic region is a city or county, the target location can be a specific address, landmark, or neighborhood within the city or county. In some embodiments, the total area of the target location is no more than 10%, 20%, 30%, 40%, or 50% of the total area of the geographic region.

The local devices can include any device capable of generating weather-related data that is located at or near the target location. For example, the local devices can each be no more than 1 mile, 2 miles, 5 miles, 10 miles, or 20 miles from the target location. Each local device can be currently at the target location, or can have been at the target location within a specified time frame (e.g., within the last 15 minutes, 30 minutes, 1 hour, 2 hours, etc.). The local devices can be wearable devices, mobile devices, computing devices, devices carried by a vehicle (e.g., an automobile, autonomous vehicle), devices associated with a building (e.g., a residence), devices at a fixed location within the environment, devices that are mobile within the environment, or any other suitable device or combination thereof.

In some embodiments, a local device can include or be operably coupled to one or more sensors that generate weather-related data. The sensors can include weather sensors configured to directly measure weather conditions, such as a temperature sensor, wind speed sensor, wind direction sensor, precipitation sensor, pressure sensor, humidity sensor, air quality sensor, and so on. Optionally, the sensors can be configured to measure a parameter that may be used to indirectly estimate weather conditions (e.g., biometric sensors that detect a user's response to weather conditions, sensors associated with climate control systems such as HVAC systems). Alternatively or in combination, a local device can include user interface components (e.g., touchscreen, keyboard) that allow a user to manually input weather-related data (e.g., the user's perception of weather conditions).

At block 506, a weather forecast for the target location is generated, based on the regional weather data and the local data. The weather forecast can include one or more weather conditions at or near the target location at a time point of interest (e.g., a current time point or a future time point). In some embodiments, the local data is analyzed to generate an estimate of local weather conditions at the target location. For example, as discussed above, the local data can include measurements of local weather conditions (e.g., temperature, precipitation, wind speed, etc.) that are directly used in the estimate. In other embodiments, the local data can include measurements of parameters that indirectly correlate with local weather conditions. For example, the local weather conditions can be estimated based on biometric data (e.g., skin temperature, perspiration), user input (e.g., users' perceptions of the weather), operation of climate control systems (e.g., climate control systems in vehicles, buildings, etc.), etc. Subsequently, the estimated local weather conditions can be combined with the regional weather data to generate the weather forecast for the target location, e.g., by weighted averaging or any other suitable technique. In some embodiments, estimates of local weather conditions from different local devices can be weighted differently, e.g., based on the expected accuracy of the estimate. For example, estimates from local devices that measure weather conditions directly can be weighted more heavily than estimates from local devices that measure weather conditions indirectly.

Subsequently, the generated weather forecast can be displayed to a user, e.g., via a graphical user interface on a mobile device or other user device. The system can also generate and display notification, alerts, recommendations, etc. based on the forecast. Optionally, the forecast can be used as input data for the other methods described herein. For example, the forecast can be used as weather data for producing a personalized weather forecast for the user, as previously discussed with respect to methods 300 and 400 of FIGS. 3 and 4.

C. Conclusion

From the foregoing, it will be appreciated that specific embodiments of the technology have been described herein for purposes of illustration, but that various modifications may be made without deviating from the disclosure. For example, while processes or blocks are presented in a given order, alternative implementations may perform routines having steps, or employ systems having blocks, in a different order, and some processes or blocks may be deleted, moved, added, subdivided, combined, and/or modified to provide alternative or subcombinations. Each of these processes or blocks may be implemented in a variety of different ways. Also, while processes or blocks are at times shown as being performed in series, these processes or blocks may instead be performed or implemented in parallel, or may be performed at different times. Further, any specific numbers noted herein are only examples: alternative implementations may employ differing values or ranges. Accordingly, the invention is not limited except as by the appended claims. Furthermore, certain aspects of the new technology described in the context of particular embodiments may also be combined or eliminated in other embodiments. Moreover, although advantages associated with certain embodiments of the new technology have been described in the context of those embodiments, other embodiments may also exhibit such advantages and not all embodiments need necessarily exhibit such advantages to fall within the scope of the technology. Accordingly, the disclosure and associated technology can encompass other embodiments not expressly shown or described herein.

We claim:

1. A system for predicting a subject's perception of weather conditions, the system comprising:
one or more processors; and
memory storing instructions that, when executed by the one or more processors, cause the system to perform operations comprising:
generating an individual profile for the subject, the individual profile including health information of the subject and calibration data indicating the subject's perception of at least one previous weather condition,
wherein the subject's perception includes a quantitative score representing a degree of perceived coldness, warmth, humidity, dryness, sunniness, or windiness, and wherein the quantitative score is determined based on the subject's biometric data collected from a sensor worn by the subject;
receiving weather data including a first weather condition for a target location;
comparing the individual profile to a plurality of different user profiles to identify one or more similar user profiles, wherein each similar user profile (1) is associated with a user having similar health information as the subject and (2) includes weather perception data indicating how the user perceived a set of second weather conditions; and
generating, based on the weather data, the calibration data, and the one or more similar user profiles, a prediction of the how the subject will perceive the first weather condition.

2. The system of claim 1, wherein the health information of the subject includes one or more of the following: age, gender, weight, height, body mass index, blood pressure, menstrual status, pregnancy status, diseases or conditions, or medical history.

3. The system of claim 1, wherein the weather data is received from a data source associated with a weather forecasting service or weather station.

4. The system of claim 1, wherein the operations further comprise generating a recommendation for the subject, based on the prediction.

5. The system of claim 4, wherein the recommendation includes a recommended action for the subject to take to prepare for the first weather condition.

6. The system of claim 1, wherein the calibration data is generated based on user input.

7. The system of claim 1, wherein the sensor includes one or more of the following: a temperature sensor, a sweat sensor, a motion sensor, an activity sensor, a heart rate sensor, a blood flow sensor, a wind sensor, a UV sensor, an oxygen sensor, or an altitude sensor.

8. The system of claim 1, wherein, for each similar user profile, the set of second weather conditions includes at least one weather condition that is the same or similar to the first weather condition.

9. The system of claim 1, wherein the operations further comprise outputting the prediction to the subject via a user device.

10. The system of claim 1, wherein the comparing and generating are performed at least partly by a machine learning model trained on the plurality of different user profiles.

11. A method for predicting a subject's perception of weather conditions, the method comprising:
generating an individual profile for the subject, the individual profile including health information of the subject and calibration data indicating the subject's perception of at least one previous weather condition,
wherein the subject's perception includes a quantitative score representing a degree of perceived coldness, warmth, humidity, dryness, sunniness, or windiness, and wherein the quantitative score is determined based on the subject's biometric data from a sensor worn by the subject;
receiving weather data including a first weather condition for a target location;
inputting the individual profile and the weather data into a machine learning model, wherein the machine learning model is trained on a plurality of different user profiles, each user profile including (1) health information for a user and (2) weather perception data indicating how the user perceived a set of second weather conditions; and
generating, based on output from the machine learning model, a prediction of the how the subject will perceive the first weather condition, wherein the prediction is generated based at least in part on the calibration data.

12. The method of claim 11, wherein the machine learning model is configured to identify one or more user profiles that are similar to the individual profile.

13. The method of claim 11, wherein the machine learning model is configured to determine associations between health information and perception of weather conditions.

14. The method of claim 11, wherein the machine learning model is trained on the individual profile.

\* \* \* \* \*